United States Patent [19]

Pouletty et al.

[11] Patent Number: 5,158,869
[45] Date of Patent: Oct. 27, 1992

[54] ANALYTE DETERMINATION USING COMPARISON OF JUXTAPOSED COMPETITIVE AND NON-COMPETITIVE ELISA RESULTS AND DEVICE THEREFORE

[75] Inventors: Philippe Pouletty, Atherton; Teresa Kendreck, San Mateo, both of Calif.

[73] Assignee: SangStat Medical Corporation, Menlo Park, Calif.

[21] Appl. No.: 549,372

[22] Filed: Jul. 6, 1990

[51] Int. Cl.⁵ .................... G01N 33/53; G01N 21/00
[52] U.S. Cl. .................... 435/7.9; 435/7.93; 435/7.94; 435/970; 435/973; 436/169; 436/170; 436/530; 436/810; 422/56; 422/58
[58] Field of Search ............ 422/56–58, 422/61; 436/169, 170, 810, 528–530; 435/7.1, 7.5, 7.93, 7.9, 7.94, 970, 973, 975, 805

[56] References Cited

U.S. PATENT DOCUMENTS

| | | | |
|---|---|---|---|
| 4,366,241 | 12/1982 | Tom et al. | 435/7 |
| 4,727,019 | 2/1988 | Valkirs et al. | 435/7 X |
| 4,748,042 | 5/1988 | Linnecke et al. | 422/56 X |
| 4,803,154 | 2/1989 | Uo et al. | 435/7.93 |
| 4,981,653 | 1/1991 | Marino | 422/56 |

FOREIGN PATENT DOCUMENTS

272134A1 9/1989 Fed. Rep. of Germany ...... 435/973

*Primary Examiner*—Esther L. Kepplinger
*Assistant Examiner*—Carol A. Spiegel
*Attorney, Agent, or Firm*—Bertram I. Rowland

[57] ABSTRACT

Apparatus and method are provided for the production of pairs of visual signals indicative of the concentration of an analyte in a sample for analysis. The apparatus comprises pairs of analyte detection regions, each pair of detection regions comprising a region for performing sandwich-type immunoassays and a region for performing competition-type immunoassays. The intensity of the visual signal in the sandwich-type imunoassay analyte detection region increases with increasing analyte concentration, whereas the intensity of the visual signal in the competition-type immunoassay analyte detection region decreases with increasing analyte concentration.

6 Claims, 2 Drawing Sheets

ANALYTE DETERMINATION USING COMPARISON OF JUXTAPOSED COMPETITIVE AND NON-COMPETITIVE ELISA RESULTS AND DEVICE THEREFORE

INTRODUCTION

1. Technical Field

The present invention relates to immunoassays for the detection of analytes.

2. Background

Immunoassays have been developed based on a number of different methodologies for detecting a wide variety of analytes. Many of these assay methods require the use of radioactivity, complex laboratory equipment, and highly trained laboratory personnel to carry out and interpret the assays. It is thus highly desirable to develop assays for the detection of analytes in which the assays can be easily performed and evaluated without the use of complex equipment or radioactivity.

Heterogenous immunoassays employing enzymatically labeled immunoreagents may be used to detect analytes without the use of complex equipment or radioactivity. Heterogenous immunoassays usually involve a ligand or antibody immobilized to a solid support. A sample containing the analyte of interest and other assay reagents is usually passed over an immobilized immunoreagent and the amount of antibody-analyte complex adhering to the support is measured by means of a label attached either directly or indirectly to one of the immunoreagents. In heterogenous assays, essential elements include the anchoring of one member of a specific binding pair to a solid support, and a means for either directly or indirectly detecting label bound to the support.

The ease of interpretation of an immunoassay is always an important consideration. Heterogenous immunoassays involving a colorimetric detection signal produced by an enzyme label generally produce a signal that varies either directly or inversely with respect to the concentration of analyte in a sample. Interpretation of assay results requires the visual analysis of changes in color intensity. Visual analysis of assay results may be subject to misinterpretation and semi-quantitative analysis of results is often extremely subjective; thus it is highly desirable to create a visual signal producing immunoassay that is extremely easy to interpret.

SUMMARY OF THE INVENTION

Methods and apparatus are provided for performing a non-instrumental assay for the detection of an analyte in a liquid sample. The apparatus comprises a bibulous membrane divided into a plurality of analyte detection regions, where a first set of regions contain immobilized analyte (or structurally related analogs) and other regions contain an immobilized specific binding member complementary to the analyte of interest. Regions containing immobilized analyte (or structurally related analogs) are used for performing competition-type or neutralization-type immunoassays in which an analyte specific immunoreagent added to the sample for analysis may bind to either the membrane immobilized analyte or to the analyte in the sample. Regions of the bibulous membrane containing the immobilized complementary specific binding pair member are used for performing a sandwich-type immunoassay in which analyte in the sample acts as a bridge between an immunoreagent and the specific binding pair member immobilized to the bibulous membrane.

The method of using the apparatus comprises the steps of mixing a sample for analysis with a solution comprising a directly or indirectly labeled immunoreagent specific for the analyte of interest, contacting the apparatus with the mixture and any other reagents, as appropriate, and so as to simultaneously produce multiple visual signals on the apparatus, at least one signal being directly proportional, and the other signal(s) being inversely proportional to the concentration of analyte in the sample.

DESCRIPTION OF THE SPECIFIC EMBODIMENTS

Figure 1:
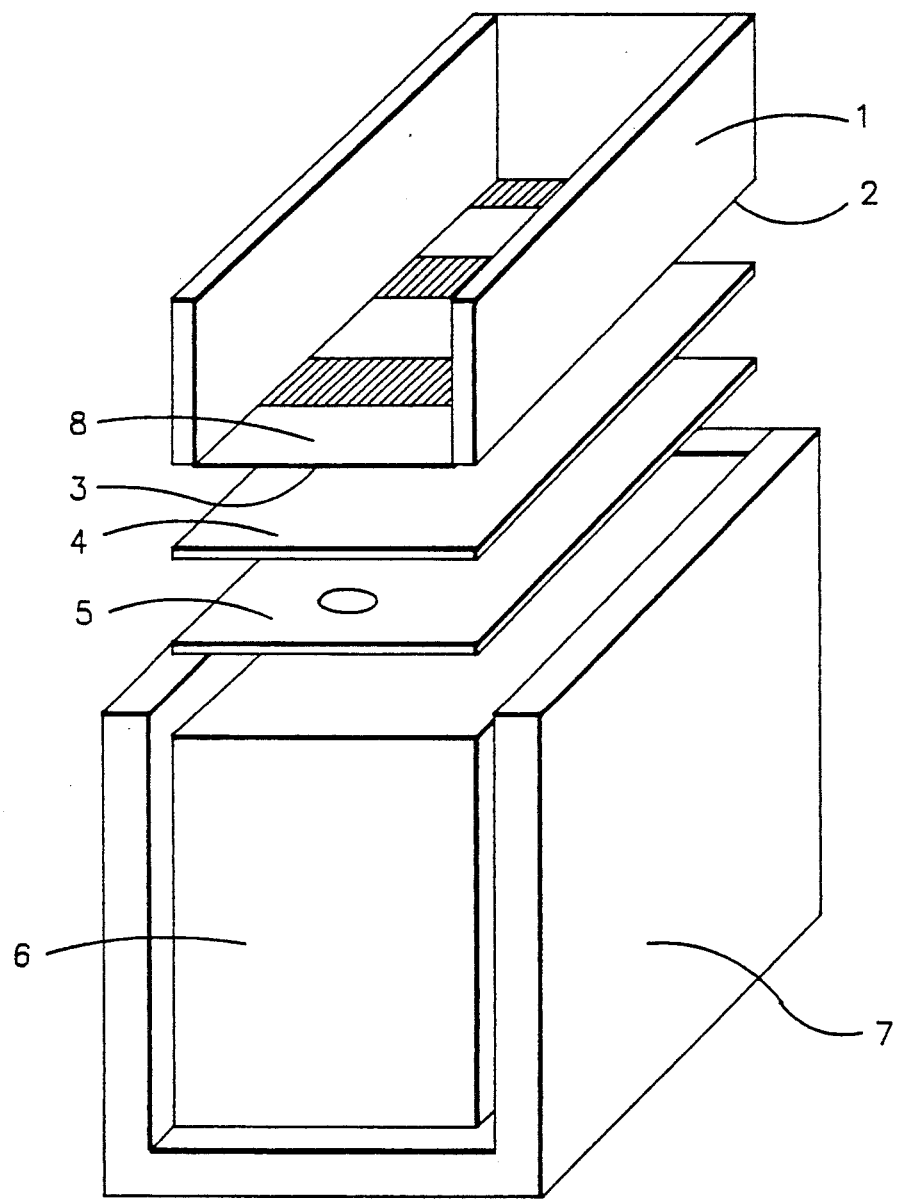
FIG. 1 is an obliquely positioned perspective view of an assay apparatus.

A solid phase immunoassay device is provided in which a pair of different related visual signals are produced in response to the same analyte when a single sample for analysis is added to the device. The device provides for the substantially concomitant performance of both sandwich-type and neutralization- or competition-type immunoassays for measuring the presence of a selected analyte in a sample. (By immunoassay is intended to include receptors other than antibodies, e.g. blood proteins, lectins and surface membrane proteins.) In the sandwich-type assay, for polyepitopic analytes, a visual signal is produced that positively (directly) correlates with the presence of the analyte of interest. In the competition-type assay, for polyepitopic analytes, a visual signal is produced that negatively (inversely) correlates with the presence of the analyte of interest. The immunoassay device is configured such that the sandwich-type immunoassays and the competition-type immunoassays are performed and may be analyzed substantially in unison by comparison of the results of the two immunoassays. Comparison of the two types of immunoassay results facilitates the semi-quantitative interpretation of data by providing for a contrast between signals produced in response to the particular level of analyte present in a sample.

Analytes suitable for detection by the subject invention are members of one or more specific binding pairs. Specific binding pairs are defined as two non-identical molecules capable of specifically non-covalently binding to each other in solution so as to form stable complexes, the binding affinity usually being greater than about $10^8 M^{-1}$. Exemplary, but not exclusive of general classes of specific binding pair interactions are ligand-receptor interactions, which are primarily exemplified by antibody-hapten or antibody-antigen interactions. Ligands (analytes) for the most part are non-proteinaceous, naturally occurring or synthetic organic molecules of from about 125 to 5,000 Dal (Dalton), peptides, proteins, lipids, oligonucleotides, and saccharides. Receptors that may be detected by the subject invention will for the most part be proteins, such as immunoglobulins, fragments thereof, particularly monovalent fragments, of immunoglobulins, e.g. Fab, Fv, etc., enzymes, naturally-occurring receptors, such as surface membrane proteins, e.g. T-cell receptors, hormone receptors, lectins, blood proteins, e.g. TBG, etc. Other examples of specific binding pairs include nucleic acids, e.g. DNA and RNA. For a disclosure of specific ligands and binding pairs see U.S. Pat. No. 3,996,349 columns 10-17, which disclosure is hereby incorporated by reference.

The subject device comprises a bibulous membrane comprising a plurality of distinct regions for the detection of analyte; each analyte detection region is used to perform either a sandwich-type or a competition-type immunoassay in which a visual signal is produced. For every analyte to be detected, the bibulous membrane comprises at least one pair of a sandwich-type and a competition-type analyte detection region. In addition, other regions may be present, such as procedural controls, e.g., having a fixed amount of label, binding to a fixed amount of label, regardless of the presence of analyte or the like.

The different regions are distinct one from the other. Individual analyte detection regions are separated from one another by any convenient means, e.g. bibulous membrane regions that are not functionalized, non-bibulous separators, non-porous adhesive tape, printed lines, etc. The subject invention may contain a single bibulous membrane or multiple bibulous membranes joined coplanarly. In embodiments of the subject device which comprise multiple coplanarly joined bibulous membranes, the membranes may be of the same or different type. Multiple bibulous membranes may be joined by a variety of means; the preferred means for joining multiple membranes is by non-porous adhesive type.

Suitable bibulous membranes for the subject device are porous layers to which a specific binding pair is capable of being immobilized while still retaining the specific binding pair members' specific binding properties. The membrane may be functionalized so as to provide for the covalent immobilization of specific binding pair members. The bibulous membrane may be composed of paper, cellulose, glass fiber, nylon, polyvinylidene difluoride (PVDF), nitrocellulose, or the like. Preferred bibulous membrane materials are nylon and nitrocellulose. Commercially available examples of such filters include IMMOBILON (Millipore), MEMTEST membrane (Memtek), BIODYNE (Pall), IMMUNODYNE (Pall), and UULTRABIND (Gelman Sciences). The pores in the bibulous membrane will usually have an average diameter in the range of about $0.1\mu$ to $10.0\mu$, usually in the range of about $0.45\mu$ to $7\mu$.

The competition-type immunoassay analyte detection regions of the subject invention comprise a specific binding pair member which is an analyte or a structural analog of the analyte, immobilized to the bibulous membrane component of the subject device. By structural analog of the analyte is intended a molecule that is not chemically identical to the analyte, but which is capable of substituting for an analyte in at least one specific binding pair interaction comprising the analyte. For example, a polypeptide consisting of amino acids 20-35 of HIV glycoprotein gp120, may act as a structural analogue for gp120 with respect to the binding interaction between gp120 and a gp120 specific monoclonal antibody if the 20-35 fragment can competitively interfere with the binding between the monoclonal antibody and natural gp120. In general, cross-reactive polypeptide fragments produced either in vitro or in vivo are suitable structural analogs for polypeptide analytes. Suitable analytes or analyte structural analogs for use in competition-type immunoassay analyte detection regions are not limited to monoclonal antibody and natural gp120. In general, polypeptide cross-reactive fragments produced either in vitro or in vivo are suitable structural analogs for polypeptide analytes. Suitable analytes or analyte structural analogs for use in competition-type immunoassay analyte detection regions are not limited to peptides, and include carbohydrates, nucleic acids, small organic molecules of less than about 5000 Dal, and the like.

The sandwich-type immunoassay analyte detection regions of the subject invention comprises a complementary specific binding pair member specific for the analyte, immobilized to the bibulous membrane component of the subject invention. The specific binding pair member immobilized to the membrane is capable of binding to analyte in samples when the analyte will also be bound to an immunoreagent specific for the analyte.

The specific binding pair member component of the sandwich-type assay analyte detection regions and the analyte (or analyte analog) of the competition-type assay analyte detection region are immobilized to the bibulous membrane by any of the generally available techniques appropriate for the specific membrane employed. The specific binding pair members to be immobilized to the membrane are immobilized in a manner such that the specific binding pair members retain their ability to bind specifically. Immobilization techniques are widely known in the art and may be found, for example, in *Practice and Theory of Enzyme Immunoassay* by Tjissen (1985), Elvsier Science Publishers, and *Antibodies: A Laboratory Manual* by Harlow and Lane (1988), Coldspring Harbor Laboratories. Preferred immobilization techniques involve the covalent attachment of specific binding pair members to the bibulous membrane. Suitable immobilization techniques also include the non-covalent immobilization of specific binding pair members to the membrane.

With mono-epitopic or haptenic analytes, some modification of the methods and the reagents employed is required in order to obtain the inverse relationship between the competitive and non-competitive assays. For example, in the competitive assay, one would prepare a polyepitopic analog of the analyte, e.g. join two or more analytes or analyte analog molecules together. The analyte would compete with the polyepitopic moiety for the immunoreagent. The polyepitopic moiety would increase binding of the immunoreagent to the membrane, so that with increasing analyte there would be diminishing signals. In the non-competitive assay, the receptor bound to the membrane would bind specifically to the analyte-immunoreagent complex, and not significantly to the analyte or immunoreagent by itself. *S. aureus* protein A or preferably a specific antibody would find use, e.g., an antibody that binds the immune complex, but not its components, antibody and hapten. With increasing analyte there would be increasing signal, to provide the inverse relationship between the two assays.

The specific binding pair member component of an individual analyte detection region may be immobilized to the bibulous membrane in a variety of immobilization patterns. By immobilization pattern, it is intended both the shape and concentration configuration of the specific binding pair member immobilized to the bibulous membrane of the subject device. All of the analyte detection regions on a given embodiment of the subject apparatus usually, though not essentially, contain specific binding pair member immobilized in the same pattern. When analyte detection regions capable of detecting different analytes are present on the same bibulous filter, it may be desirable to have a different specific binding pair immobilization pattern for each analyte; however, the competition-type analyte detection region and the sandwich-type analyte detection region specific binding pair members specific for the same analyte are preferably present in the same pattern. In general, specific binding pair members will be immobilized as circular spots; however, the shape of the spot may be other than circular.

The specific binding pair member forming the spot may be of a uniform or variable concentration. An embodiment of the subject device of particular interest involves analyte detection regions in which the specific binding pair member is immobilized to the membrane in an annular or circular spot such that the specific binding pair member is arranged in a non-linear radial concentration gradient where the concentration decreases with increasing distance from the center of the spot. The advantages of this particular specific binding pair member immobilization pattern include ease of interpretation of test results; the advantages are described in detail in U.S. patent application Ser. No. 07/444,814 which is hereby incorporated by reference.

The bibulous membrane containing the analyte detection regions is preferably, though not essentially, a component of an apparatus designed to facilitate the performance of immunoassays, henceforth called an immunoassay cartridge. Such cartridges serve to eliminate the need for complex machines for washing, measuring, and analyzing that are normally employed with many immunoassays. Exemplary, though not exclusive of such immunoassay cartridges is the immunoassay device described in U.S. patent application Ser. No. 07/444,814, incorporated herein by reference.

The device comprises a holder which may be conveniently molded of plastic. The bottom layer may be an absorbent layer for receiving fluid. A flow restricting layer may be supported by the absorbent layer, which in turn supports the membrane layer. The holder provides a well around the membrane into which the sample may be added.

Other configurations may be employed, such as chromatographic or bibulous strips, disks or the like, where the sample may be applied at one end and allowed to migrate from the site of contact with the strip, extending through the regions, so long as the design provides that all of the regions are exposed to the same concentration of analyte. One could provide for spokes radiating from the sample application site, a plurality of parallel stripes, etc.

The subject device may detect one or more analytes in a given sample. For each analyte to be detected in a given sample, the embodiment of the subject device contains at least one pair of analyte detection regions, a sandwich-type analyte detection region and a competition-type analyte detection region. Multiple analyte detection region pairs for the detection of the same analyte may be present on a given embodiment of the subject device, where such pairs will normally differ with respect to one another by the concentration of specific binding pair member in each analyte detection region. By providing analyte detection regions with a variety of different specific binding pair member concentrations, a given embodiment of the subject device may measure the quantity of analyte present in a sample over a wider range of concentrations than can be achieved with a single pair of analyte detection regions.

The subject invention further comprises methods for using the subject immunoassay device. A sample, optimally subject to pair treatment is mixed with a reagent solution, followed by applying the mixture to the subject apparatus. The sample solution is absorbed by the membrane and an absorbent layer in fluid receiving contact with the membrane. Various labels may be employed, where the labels may be observed directly, e.g., fluorescein, dyed microbeads or particles, colloidal metals, e.g., gold; or after a further step, e.g., enzymes, with the addition of substrate and any cofactors or other component of the enzyme reaction. With the enzymes, signal development solution is then added. Addition of the signal development solution initiates the formation of color development in the analyte detection regions. The signals formed in the analyte detection regions are compared with one another and the analyte(s) concentration in the sample determined.

By employing the subject system and having a plurality of regions which provide different levels of signal with different levels of analyte, one can usually obtain a fairly accurate determination of concentration, usually within 5–20 $\mu$g/ml of analyte. Thus one could imagine a system where the analyte will vary in the range of 0–50 $\mu$g/ml. One could provide for five wells for each type of assay, where the concentration of reagents is selected to provide different signals at the concentrations: <5 $\mu$g/ml; 5–10 $\mu$g/ml; 10–20 $\mu$g/ml; 20–40 $\mu$g/ml and >40 $\mu$g/ml. With the analyte in the range 10–20 $\mu$g/ml, one would expect to see for the competitive assays dark; dark; light; none; none; while with the non-competitive assay: none; light; dark; dark; dark. Thus, by having a direct comparison with the wells of the same concentration level in juxtaposition, either tandem across the strip or side-by-side, one can readily read the concentration.

For polyepitopic analytes the labeled specific binding pair member or immunoreagent is the same in the competitive and non-competitive assays. Thus, for a ligand analyte, e.g., antigen, the immunoreagent is conveniently a label, e.g., an enzyme conjugated to a receptor, e.g. an antibody. One uses a single reagent solution at a single concentration to obtain the inverse result, depending whether the region has ligand or receptor immobilized.

Enzymes which have found application in immunoassays may find application in the subject invention. The enzyme should be stable, have a high turnover rate, have a substrate which provides an insoluble intense colored or black product, and be easily conjugated without significant loss of activity.

Exemplary, but not exclusive of suitable enzymes for use as tags are alkaline phosphatase, $\beta$-galactosidase, horseradish peroxidase, $\beta$-glucuronidase, $\beta$-glucose-6-phosphate dehydrogenase and $\beta$-amylase.

The specific binding pair member which is complementary to the analyte/anti-analyte may be covalently bonded to the enzyme label by any convenient linking member, may be covalently bonded to a non-enzymatic label, where a reagent is provided comprising a receptor for the non-enzymatic label covalently linked to an enzyme or may be unlabeled, where an antibody for the anti-analyte conjugated to an enzyme is provided. The immunoreagent may, therefore, have one or more components in addition to the enzyme substrate(s). In the second and third situation the anti-analyte will be referred to as indirectly labeled.

By having separate reagents, the assay can be expanded into an additional step, which allows intermediate washing to remove non-specifically bound anti-analyte from the bibulous layers. Alternatively, the reagents may be precombined or combined in the assay medium. By having two reagents, one may increase the level of enzyme present or absent for each analyte molecule, simplify conjugation, and the like.

Exemplary, but not exclusive of specific binding pairs suitable for indirect labeling with enzyme tags is the biotin/avidin (or biotin/streptavidin) pair. In a preferred embodiment of the subject invention, biotin is covalently attached to an analyte-specific monoclonal antibody (anti-analyte-biotin) and streptavidin is covalently attached to alkaline phosphatase.

When the subject device contains analyte detection regions suitable for measuring the quantity of more than one analyte present in a given sample, the reagent solution used in assays with the subject device will preferably contain multiple immunoreagents specific for each analyte to be measured. The enzyme labels on the different immunoreagents may be the same or different. When multiple immunoreagents are present, they may be either directly or indirectly labeled. When indirect labeling of multiple immunoreagents is employed, the same enzyme label is usually used for all of the immunoreagents in the reagent solution.

In addition to an immunoreagent and enzyme label, the reagent solution added to the sample may also comprise appropriate salts, buffers, and proteins that facilitate specific binding pair interactions and the activity of the enzyme label.

In the final stage, usually after washing the bibulous layer, the signal detection solution is added. The signal detection solution comprises chromogenic substrates specific for each enzyme label in the reagent solution. Preferred chromogenic substrates are leuco dyes, colorless prior to interaction with their cognate enzyme, and produce stable, insoluble, and colored reaction products.

The reagent solution employed in the subject method may be stored in an apparatus that serves to collect sample for analysis, mix the sample with the reagent solution, and dispense the sample-reagent solution mixture to the subject device. A preferred embodiment of such a device is the collector-diluter-dispenser described in U.S. patent application Ser. No. 07/444,814, still pending.

The subject invention is able to measure analyte concentration over a wide range of concentrations by varying the concentration and/or volume of the immunoreagent and/or the amount per unit area of the specific binding pair member immobilized to the competition-type analyte detection regions and the sandwich-type analyte detection region. Incubation times of the various steps will also affect the dynamic range of the assay. Analyte detection regions employing the same specific binding pair member but in a variety of concentrations are normally present on the same bibulous membrane.

Preferred concentrations of immunoreagent and specific binding pair members will produce assay test results that result in the formation of a visual signal in the analyte detection regions over the analyte concentration range entered, so that one will obtain a clear visual contrast where the analyte concentration falls into the particular concentration range of the individual detection region. Preferred concentrations and volumes of immunoreagent and immobilized specific binding pair members may be found by routine optimization experiments.

Figure 2:
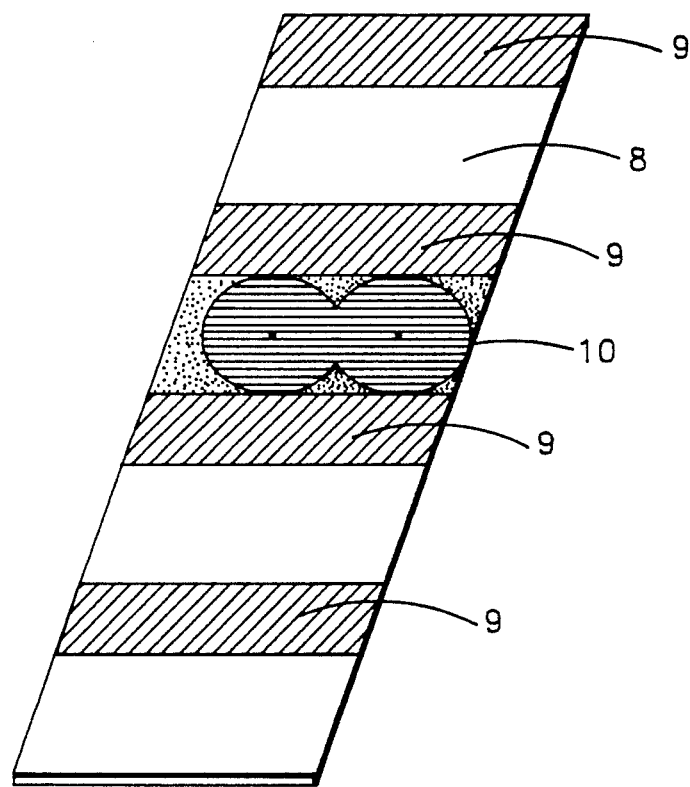
FIG. 2 is a plan view of the porous reactive filter.

As shown in FIGS. 1 and 2, the assay apparatus has a plurality of layers in housing 2, which housing a comprises upper portion 1 and lower portion 7. In descending order the principal layers are a porous reactive filter 3, divided into regions by tape 9, each of the regions containing members of specific binding pairs, which form rings 10 as a negative or positive result in the assay, a porous separation layer 4, a flowrate control layer 5, and a waste fluid receiving pad 6. The porous reactive filter 3 will have pores in the range of about 0.1 to 10μ. Each of the regions 8 of the porous reactive filter 3 may be divided in half by a hydrophobic band filter 3 impregnated in the porous reactive filter 3, e.g., wax, polyethylene or the like, to separate region 8 into two subregions, providing for the different specific binding members which respond inversely to analyte.

It is desirable to provide the subject device in the form of a standardized kit containing the subject device, all reagents required for using the subject device, and appropriate additional tools for using the subject device. Standards for analysis may also be included with a kit. By providing a kit, assays performed using the subject device may be carried out more rapidly and reproducibly.

EXPERIMENTAL

Microalbuminuria Test

A diagnostic test for microalbuminuria employing the subject invention is provided. The test measures the concentration of human albumin in a urine specimen. The test device comprises a competitive type analyte detection region in which human albumin is immobilized to a nitrocellulose filter membrane in a ring shaped spot. The test device also comprises a sandwich-type analyte detection region in which a first monoclonal antibody, specific for human albumin is immobilized to the filter in a ring shaped spot. The nitrocellulose filter containing the two analyte detection regions is a component of an immunoassay diagnostic cartridge of the type described in U.S. patent application Ser. No. 07/444,814. The cartridge is configured so that samples prepared for analysis are added directly onto the filter, and the test results are monitored by observing the filter without any need for disassembling the cartridge.

1) Microalbuminuria STAT-test

In the first miniwell of a STAT cartridge, human albumin is coated on the membrane using a ring pattern; human albumin (from Sigma) is coated at a concentration of 1 mg/mL in 0.2M PBS pH 7.4.

In the second miniwell, goat anti-human albumin antibody (American Qualex) is coated on the membrane using a ring pattern; the antibody is coated at a concentration of 0.1 mg/mL in 0.2M PBS pH 7.4.

After 30 minutes drying at 37 ° C., the membrane is blocked by soaking 15 minutes in 0.1M PBS (phosphate buffered saline) pH 7.4 with 1% casein w/w (Sigma) and 0.1% TWEEN 20 (Sigma) and drying 30 min at 37° C.

Assay Protocol

The urine sample is collected using a Dipette. The nib of the Dipette contains in dry form 2 μg of anti-human albumin biotin antibody conjugate (biotin/antibody molar ratio: 25). After the urine sample has been absorbed, the Dipette is crushed, the nib falls into a solution of alkaline phosphatase streptavidin conjugate (Tago), diluted 1:200 in 0.1M carbonate-bicarbonate buffer pH 9.5 with 1% casein w/w and 0.1% Tween 20 (Sigma). After 30 seconds of gentle agitation, 5 drops (approximately 250 μl ) of the urine sample/anti-albumin-biotin conjugate/alkaline phosphatase streptavidin conjugate solution is dispensed to the STAT cartridge.

After complete draining, 1 mL of washing solution ($H_2O$) is added to the STAT cartridge.

After complete draining, 250 μl of BCIP/NPT (Kirkgaard and Perry Laboratories) (bromochloroindoxylphosphate/nitrobluetetrazolium) solution is added. The results are read after 3 minutes (Table 1):

TABLE 1

| | Interpretation of test results | | | | |
|---|---|---|---|---|---|
| | Albumin concentration | | | | |
| Test result | <5 mg/μl | 5–10 μg/ml | 10–20 μg/ml | 20–40 μg/ml | >40 μg/ml |
| First miniwell colored rings | Dark blue | Dark blue | Dark blue | Light blue | None |
| Second miniwell colored rings | None | Light blue | Light blue | Dark blue | Dark blue |
| Interpretation | Negative | Negative | Negative | Positive | Positive |

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for determining a polyepitopic analyte in a sample, wherein said analyte is a member of a specific binding pair, said method employing a bibulous membrane having at least a pair of juxtaposed first and second analyte detection regions capable of receiving portions of the same sample, wherein the first and second regions comprise first and second reagents, said first reagent comprising an immobilized specific binding member which specifically binds to said analyte and said second reagent comprising immobilized analyte or a structurally related analog thereof, respectively, and employing an immunoreagent comprising a label capable of providing a detectable signal and a specific binding pair member which specifically binds to said analyte, such that the amount of said immunoreagent which binds to said first region is directly proportional to the amount of said analyte present in said sample and such that the amount of said immunoreagent which binds to said second region is inversely proportional to the amount of said analyte present in said sample, so that the signal intensity of a visual signal produced in said first and second regions will be the same or different depending on the amount of said analyte in said sample, said method comprising:

contacting said sample with said immunoreagent to form an assay mixture;
   contacting said assay mixture to said bibulous membrane, wherein reaction occurs between said immobilized first and second reagents, said analyte and said immunoreagent; and
   detecting the amount of said analyte in said sample by comparing the signal intensity produced in said first and second regions.

2. The method according to claim 1, wherein said immunoreagent comprises an enzyme as said label.

3. The method according to claim 1, wherein said bibulous membrane comprises a plurality of paired and juxtaposed first and second regions, wherein each said first region comprises a different concentration of the immobilized specific binding pair member which specifically binds to said analyte and each corresponding juxtaposed said second region comprises a corresponding different concentration of the immobilized analyte or analog thereof such that the plurality of paired and juxtaposed first and second regions produce a gradation of signal intensities, directly and indirectly proportional, respectively, to a preselected range of analyte concentration.

4. A diagnostic device for determining a polyepitopic analyte, wherein said analyte is a member of a specific binding pair, said device comprising:

a bibulous membrane having at least three paired and juxtaposed first and second analyte detection regions capable of receiving portions of the same sample, wherein the first and second regions comprise first and second reagents, respectively, where said first reagent comprises an immobilized specific binding member which is capable of specifically binding to said analyte and said second reagent comprises immobilized analyte or a structurally related analog thereof,
   wherein the paired and juxtaposed first and second regions have corresponding concentrations of immobilized reagents such that the paired and juxtaposed first and second regions are capable of producing a gradation of signal intensities, directly and indirectly proportional, respectively, to a predetermined range of analyte concentrations, when said device is contacted with a test solution comprising a sample to be tested and an immunoreagent comprising a label capable of providing a detectable signal and a specific binding pair member which specifically binds to said analyte.

5. The device according to claim 4, wherein said first regions comprise a specific binding pair member capable of specifically binding to said analyte and said second region comprises a structurally related analog of said analyte.

6. The device according to claim 4, comprising a fluid adsorbing layer in fluid receiving relationship to each of said regions of said bibulous membrane for receiving waste fluid.

* * * * *